United States Patent [19]
Haehn

[11] Patent Number: 5,316,744
[45] Date of Patent: May 31, 1994

[54] ABSORPTION COLUMN WITH EXTERNAL MIXING FOR ABSORPTION OF ACETYLENE

[75] Inventor: Peter-Clemens Haehn, Geretsried, Fed. Rep. of Germany

[73] Assignee: Linde Aktiengesellschaft, Wiesbaden, Fed. Rep. of Germany

[21] Appl. No.: 46,298

[22] Filed: Apr. 14, 1993

Related U.S. Application Data

[60] Division of Ser. No. 980,886, Nov. 24, 1992, which is a continuation of Ser. No. 933,538, Aug. 24, 1992, abandoned.

[30] Foreign Application Priority Data

Aug. 23, 1991 [DE] Fed. Rep. of Germany ....... 4127987

[51] Int. Cl.$^5$ .......................... B01F 3/00; B01D 11/04
[52] U.S. Cl. ..................................... 422/257; 422/211; 422/224; 422/256; 202/176; 203/DIG. 6; 203/DIG. 9; 261/114.1; 261/18.1
[58] Field of Search .............................. 422/255–257, 422/224, 211; 261/114.1, 118.1; 202/176; 203/DIG. 6, DIG. 9

[56] References Cited

U.S. PATENT DOCUMENTS

| | | | |
|---|---|---|---|
| 3,605,388 | 9/1971 | Zuiderweg et al. | 261/114.1 |
| 4,415,508 | 11/1983 | Aida et al. | 261/114.1 |
| 4,655,798 | 4/1987 | Ruch et al. | 55/64 |

FOREIGN PATENT DOCUMENTS

3833795 4/1990 Fed. Rep. of Germany .

Primary Examiner—Robert J. Warden
Assistant Examiner—Robert Carpenter
Attorney, Agent, or Firm—Millen, White, Zelano, & Branigan

[57] ABSTRACT

In the absorption of acetylene from a crude gas mixture containing mostly $C_2$ hydrocarbons by scrubbing with an absorbing agent, an externally produced mixture of about 10–70% by weight acetylene-free $C_2$ hydrocarbons and about 30–90% by weight absorption agent is introduced in the absorption column, in order to prevent the formation of foam. The mixture is produced in a static mixer outside the absorption column, and is supplied from outside the column to a mixing tank installed between two plates within the column.

7 Claims, 1 Drawing Sheet

ABSORPTION COLUMN WITH EXTERNAL MIXING FOR ABSORPTION OF ACETYLENE

CROSS-REFERENCE TO RELATED APPLICATION

This application is a divisional of application Ser. No. 07/980,886, filed Nov. 24, 1992, which, in turn, is a continuation of application Ser. No. 07/933,538, filed Aug. 24, 1992, now abandoned.

BACKGROUND OF THE INVENTION

This invention relates to a gas absorption process and apparatus, particularly for scrubbing acetylene out of a crude gas mixture containing mostly $C_2$ hydrocarbons.

The invention is especially directed to an improvement in the operation of a plate column, wherein the crude gas mixture is fed into the lower zone of the absorption column; fresh or regenerated absorption agent is fed to the upper zone of the absorption column; loaded absorption agent is drawn off the bottom of the absorption column and is fed to a regeneration stage; an acetylene-free product gas stream is withdrawn from the head of the absorption column, optionally after separation and recycling of a reflux condensate to the absorption column, and wherein a substantially acetylene-free liquid $C_2$ stream is introduced into the absorption column between the respective feed points for the crude gas mixture and the absorption agent.

In the extraction of ethylene from a thermally cracked cut of hydrocarbons, a crude gas mixture is obtained containing mostly $C_2$ hydrocarbons (ethylene, acetylene and optionally ethane). Besides the $C_2$ hydrocarbons, the crude gas mixture may also contain $C_3$ hydrocarbons and/or methane. Acetylene is conventionally removed from this crude gas mixture by scrubbing with an absorption agent selective for acetylene; however.

The absorption agent tends to foam under normal operating conditions, which results in downtime and/or acetylene escaping into the product gas.

The formation of both hydrocarbon-rich and hydrocarbon-poor liquid phases, in addition to the vapor phase, are generally responsible for the foam. These two liquid phases are formed when the saturation limit of the absorption agent is exceeded relative to the hydrocarbons present. But foam formation can also occur far below the saturation limit in the absorption column, particularly under unstable operating conditions.

In this connection, EP-B 158 280, corresponding to U.S. Pat. No. 4,655,798, describes a process intended to prevent foam formation by providing an additional feed of a substantially acetylene-free liquid $C_2$ stream into the absorption column. From DE-OS 38 33 795, another process is known wherein the gaseous stream withdrawn from the head of the absorption column, is partially condensed and is recycled into the absorption column and a branched partial stream of the reflux condensate is introduced in the absorption column between the feed points for the crude gas mixture and for the absorption agent. Both of these processes, however, do not solve the problem of foam formation entirely satisfactorily.

SUMMARY OF THE INVENTION

An object of this invention, therefore, is to provide a process and apparatus leading to a diminution or complete prevention of foam formation.

Upon further study of the specification and appended claims, further objects and advantages of this invention will become apparent to those skilled in the art.

These objects are achieved according to the invention by mixing, at a location externally of the column: (a) a substantially acetylene-free liquid $C_2$ stream and/or said partial stream of the reflux condensate with (b) the absorption agent, and introducing the resultant mixture into the absorption column.

For the process according to the invention, all absorption agents are suitable which exhibit a selective solubilizing power relative to acetylene, such as, for example, N-methylpyrrolidone (NMP) or dimethylformamide (DMF).

The crude gas mixture containing mostly $C_2$ hydrocarbon generally contains on a percent by volume basis about 0.5 to about 4.0 acetylene and about 95.0 to about 99.0 other $C_2$ hydrocarbons.

The substantially acetylene-free liquid $C_2$ stream generally contains in percent by weight basis, less than about 5 ppm, especially less than about 0.5 ppm, acetylene.

The composition partial stream of the reflux condensate is generally in principle identical with the composition of the overhead product stream.

The temperature and pressure conditions in the column are generally about 210 to 283, preferably 238° to 273° K. and about 6.0 to 30.0, preferably 15.0 to 30.0 bar.

Surprisingly, it has been shown that a foam formation can be prevented by external mixing outside the absorption column and the introduction of the mixture in the absorption column. In addition, the consumption of resources can be lowered by the process according to the invention because of the evaporation of the $C_2$-hydrocarbons. The evaporation of the $C_2$-hydrocarbons contributes to a decreasing of the absorption temperature in the column and consequently the temperature of the absorption agent drops.

As a result, the solubilizing power of the absorption agent is further increased relative to the acetylene. The increasing of the solubilizing power of the absorption agent leads to a decreasing of the required amount of absorption agent in the column, respectively, the scrubbing process. Further, an advantageous operation of the absorption process in the column is assured due to the following facts: reducing the absorption temperature, minimizing the foaming risk and decreasing the additional ethylene absorption because of the reduced amount of absorption agent.

Besides the addition of the mixture into the absorption column according to the invention, a partial stream of the reflux condensate and/or a substantially acetylene-free $C_2$ stream can also be fed into the absorption column. Also, reflux condensate is optionally but preferably passed into the head of the absorption column, but in this case, it is preferred to dispense with any addition of unmixed feed of a partial stream of the reflux condensate or a substantially acetylene-free $C_2$ stream to the absorption column.

The mixing of the $C_2$ stream and the absorption agent advantageously is performed preferably in a static mixer outside the absorption column. In this way, a homogeneous mixture can be obtained. By "static mixer" is meant a mixer without any agitating or moving parts. In principle, a dynamic mixer, e.g., a tank with an agitator, can be used.

In further development of the process according to the invention, the absorption agent in the column accumulates in a zone located between two plates, and the mixture is injected into this zone, hereinafter referred to as "internal mixing zone". Thus, there is obtained an immediate and thorough mixing of the mixture with the absorption agent within the absorption column. The mixture is preferably introduced into the absorption column between the respective feed points for the crude gas mixture and the absorption agent, and it is especially preferred for the mixture to be introduced into the lower third of the absorption column.

In a still further development of the invention, the externally produced mixture preferably has a temperature which is below the temperature of the absorption agent in the column, into which the mixture is introduced. In this way, the absorption agent in the absorption column can be subcooled, resulting in an increase in the solubilizing power of the absorption agent relative to acetylene.

For example, it is preferred that the temperature of the externally produced mixture is about to 1° to 20°, preferably 2° to 15° below the temperature of the absorption agent in the column.

The mixture can also be split into a plurality of streams and passed into the absorption column at different locations and with different temperatures so as to control the temperature profile in the scrubbing column.

In a further embodiment of the invention, the internal mixing zone and the plate downcomers, which are between the individual plates can be filled with packing, e.g., structured or non-structured packing. In this way, on the one hand, the gas-liquid contact is more efficient, and on the other hand, the mixing of the liquids is improved.

According to the invention, the mixture contains between 10 and 70% by weight, preferably between 30 and 50% by weight of the substantially acetylene-free $C_2$ hydrocarbons, the remainder being the absorption agent.

In the apparatus aspect of the invention, there is provided an absorption column having a plurality of plates, a feed pipe for the crude gas mixture, a feed pipe for the regenerated absorption agent, an outlet for the acetylene-free product gas stream, an outlet for the loaded absorption agent, and optionally a feed pipe for a partial stream of the reflux condensate.

According to the invention, an internal mixing chamber open on top is installed between two plates and a feed pipe for the mixture leads into or above said chamber. The feed pipe is directly or indirectly connected to mixing means outside of the column for mixing substantially acetylene-free liquid $C_2$ stream and/or the partial stream of the reflux condensate with the absorption agent.

The feed pipe of the mixture can be branched into a plurality of pipe ends in the mixing tank. In this way, a better distribution of the mixture in the pool of absorption agent can be obtained. Advantageously, the feed pipes of the mixture in the mixing chamber and/or the pipe ends are also provided with outlet orifices preferably on their top side. The outlet orifices produce a finely divided addition of the mixture in the absorbing agent.

In still further development of the invention, a static mixer is incorporated in the feed pipe for the mixture outside the absorption column. The static mixer produces a homogeneous mixture of $C_2$ hydrocarbons and absorbing agent.

BRIEF DESCRIPTION OF THE DRAWING

Various other objects, features and attendant advantages of the present invention will be more fully appreciated as the same becomes better understood when considered in conjunction with the accompanying drawing, in which like reference characters designate the same or similar parts throughout the several views, and wherein.

DETAILED DESCRIPTION OF THE DRAWING

Figure 1:
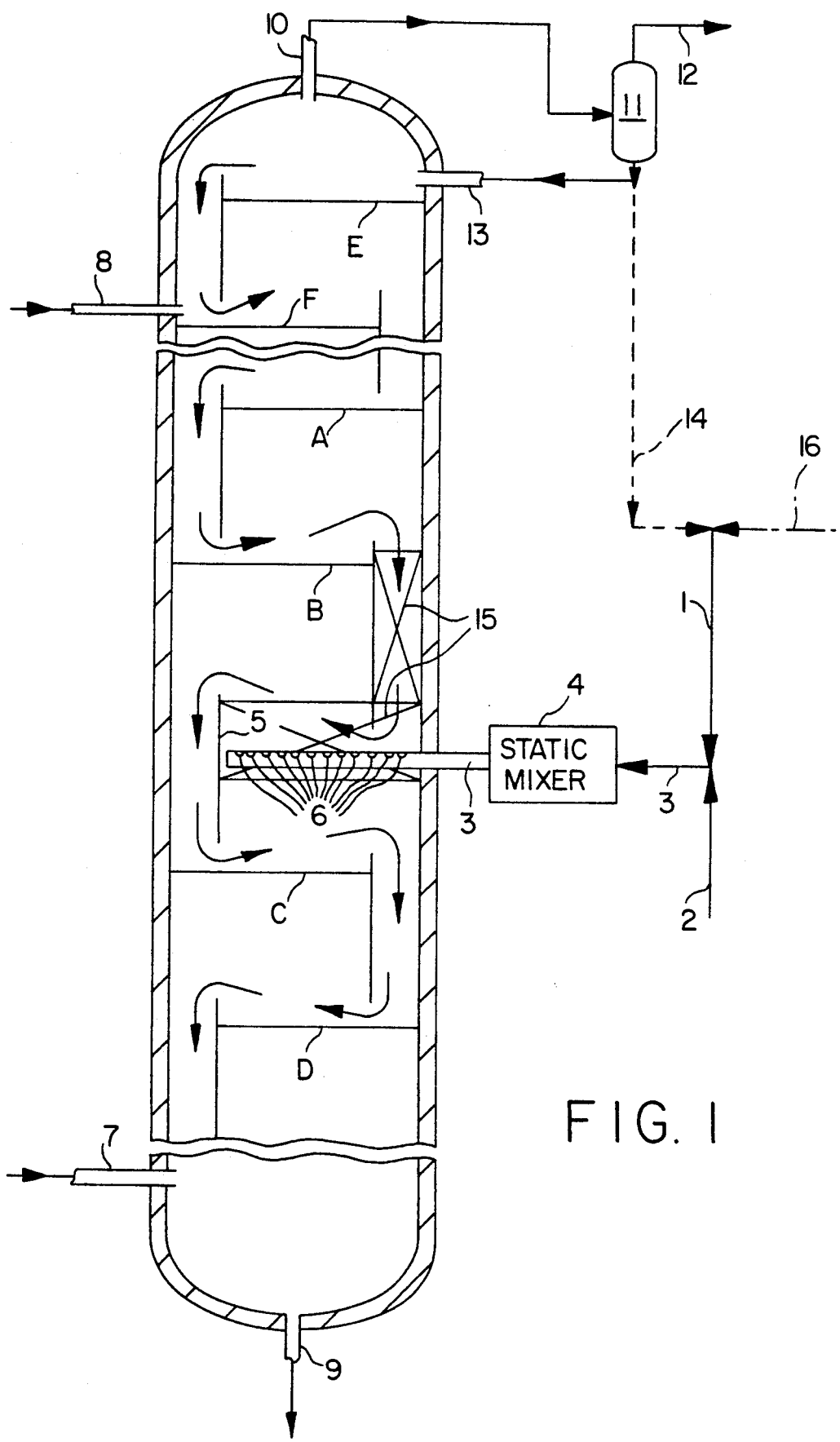
FIG. 1 is a front vertical schematic view of an absorption column according to the invention.

In FIG. 1, there is illustrated plates A, B, C, D, E and F, which, for example, may be bubble plates or sieve plates. Offset downcomers are installed in the absorption column between the plates. The absorption agent falls countercurrently to the rising gas from one plate to the underneath plates by the associated plate downcomer. The direction of the absorption agent flowing downward in the absorption column is represented by arrows. At the bottom of the column, crude gas is passed into the column through feed gas inlet pipe 7, and loaded absorption agent is withdrawn through outlet pipe 9 for the loaded absorption agent. At the top of the column, fresh or regenerated absorption agent is fed into the column in feed pipe 8; and, through outlet pipe 10 at the top of the column, a substantially acetylene-free gas stream is withdrawn. This gas stream is then passed into condenser 11, wherein a reflux condensate is obtained at the bottom of the condenser, and a substantially acetylene-free product gas stream 12 is withdrawn from the top of the condenser. The reflux condensate is passed into reflux condensate pipe 13, which enters the top of the column. An optional branch of this reflux condensate is passed via a conduit 14 positioned outside of the column to below the junction of the reflux condensate pipe 13 with the top of the column. The optional partial stream of reflux condensate is then passed into pipe 1, either by itself or jointly with substantially acetylene-free liquid $C_2$ stream in conduit 16. Alternatively, none of the reflux condensate is branched into pipe 1, and only substantially acetylene-free $C_2$ stream is mixed with the absorption agent, as described in detail below.

A substantially acetylene-free $C_2$ stream in the liquid phase under a pressure of about 0.1 to 1 bar above the column pressure at the inlet point of the mixture, and about a temperature of about $-10°$ to $-55°$ C., depending on the pressure, in pipe 1 is joined together with absorption agent from pipe 2 and the mixture is passed into pipe 3. The absorption agent in pipe 2 is branched, for example, from regenerated absorbing agent recycled to the absorption column. The absorption agent is generally at a temperature of about 1° to 15°, preferably 2° to 11° above the temperature of the crude gas stream, and is present under sufficiently high pressure to be mixed with the $C_2$ stream.

The mixture of $C_2$ hydrocarbons and absorption agent in pipe 3 is homogeneously mixed in an external static mixer 4 which is a mixer with static fittings, e.g., a spiral coil.

From the static mixer, the mixture is passed by pipe 3 into internal mixing chamber 5 provided with packing. Mixing chamber 5 is associated with a downcomer provided with packing installed between trays B and C. Feed pipe 3 is provided with outlet openings inside the mixing tank on its top side, by which the mixture is introduced in finely divided droplets into the absorption agent accumulated in the mixing tank. By virtue of a lower temperature of the mixture, it subcools the absorption agent in the mixing chamber 5. The liquid absorption agent is passed from mixing chamber 5, open on top, by the downcomer of mixing tank 5 between plates B and C to tray C, to the plates below.

The invention can suitably be used in the absorption of all acetylenes from hydrocarbon streams, for example, in the removal of methyl acetylene from a $C_3$ stream.

It is also contemplated that this invention will be useful in any gas absorption column, in order to prevent foaming.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 27 987.5, filed Aug. 23, 1991, are hereby incorporated by reference.

Specific Example

A crude gas stream with a temperature of 225.0° K. and a pressure of 10.0 bars containing

| | |
|---|---|
| 1.0 vol. % | $C_2H_2$ |
| 84.0 vol. % | $C_2H_4$ |
| 14.0 vol. % | $C_2H_6$ and |
| 1.0 vol. % | $C_{3+}$ | is fed into the lower zone of the absorption column. A regenerated DMF stream as absorption agent is introduced into the upper zone of the absorption column with a temperature of 238.0° K. and a pressure of 10.2 bars. Loaded DMF is withdrawn from the bottom of the absorption column with a temperature of 243.0° K. and a pressure of 10.3 bars. An acetylene-free product gas stream containing

| | |
|---|---|
| $C_2H_2$ | <1 ppm |
| $C_2H_4$ | 85.7 vol. % |
| $C_2H_6$ | 14.3 vol. % | is withdrawn with a temperature of 223.0° K. and a pressure of 10.0 bars from the head of the absorption column. A reflux condensate of the overhead product gas stream with a temperature of 223.0° K. and a pressure of 10.5 bars is passed to the head of the absorption column.

According to the invention, a partial stream of the reflux condensate with a temperature of 223.0° K. and a pressure of 10.5 bars is mixed outside the absorption column with a DMF stream with a temperature of 238.0° K. and a pressure of 10.5 bars. After mixing thoroughly the acetylene-free $C_2$ stream (in this example the partial stream of the reflux condensate) and the DMF stream in a static mixer the resultant mixture is introduced in the mixing chamber of the absorption column. Alternatively, an external liquid acetylene-free $C_2$ stream can be used instead of the partial stream of reflux condensate. Such an external substantially acetylene-free $C_2$ stream can be, for example, pure ethylene, e.g., from a $C_2$ cycle of the petrochemical plant. An external substantially acetylene-free liquid $C_2$ stream must be used in the case of no leading back a reflux stream to the head of the absorption column.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An absorption system suitable for removing acetylene from a crude gas containing mostly $C_2$ hydrocarbons including acetylene, said absorption column comprising a plurality of plates, a feed pipe at the bottom of the column for crude gas, a feed pipe at the top of the column for fresh or regenerated absorption agent, an outlet at the top of the column for a substantially acetylene-free gas stream, an outlet at the bottom of the column suitable for loaded absorption agent an internal mixing chamber (5), open on the top, installed between two plates (B, c), a feed pipe (3) suitable for a mixture of absorption agent and substantially acetylene-free liquid $C_2$ stream and/or a partial stream of reflux condensate recovered from a condenser in communication with said outlet at the top of the column, said feed pipe (3) leading into said internal mixing chamber, external mixing means outside of said column suitable for mixing said substantially acetylene-free liquid $C_2$ stream and/or the partial stream of the reflux condensate with the absorption agent, and an opposite end of said feed pipe (3) in communication with said external mixing means.

2. An absorption system to claim 1, wherein said feed pipe (3) comprises branched ends located in the internal mixing chamber.

3. An absorption system according to claim 1, wherein said feed pipe (3) in the internal mixing chamber comprises a plurality of outlet orifices on the upper side of said feed pipe.

4. An absorption system according to claim 2, wherein the branched ends of the feed pipe (3) in the internal mixing chamber comprises a plurality of outlet orifices on the upper side of said feed pipe.

5. An absorption system according to claim 1, wherein said external mixing means is a static mixer.

6. An absorption system according to claim 3, comprising a feed pipe suitable for a partial stream of the reflux condensate leading from said condenser into said mixing chamber.

7. An absorption system according to claim 1, further comprising a downcomer leading into said internal mixing chamber, said downcomer and said internal mixing chamber containing packing therein.

* * * * *